United States Patent [19]

Baureis

[11] Patent Number: 4,716,766

[45] Date of Patent: Jan. 5, 1988

[54] METHOD OF EVALUATING THE PEEL STRENGTH OF THE PLASTIC SLIDING LAYER OF A LAMINATE FOR SLIDING SURFACE BEARINGS

[75] Inventor: Hans-Paul Baureis, Dielheim-Horrenberg, Fed. Rep. of Germany

[73] Assignee: Kolbenschmidt Aktiengesellschaft, Neckarsulm, Fed. Rep. of Germany

[21] Appl. No.: 881,881

[22] Filed: Jul. 3, 1986

[30] Foreign Application Priority Data

Jul. 13, 1985 [DE] Fed. Rep. of Germany ....... 3525068

[51] Int. Cl.$^4$ ............................................. G01N 3/08
[52] U.S. Cl. .................................................... 73/827
[58] Field of Search ................... 73/826, 827, 834, 835

[56] References Cited

U.S. PATENT DOCUMENTS

| | | | |
|---|---|---|---|
| 2,989,865 | 6/1961 | Belfour | 73/827 |
| 3,580,065 | 5/1971 | Strittmater et al. | 73/827 |
| 4,396,658 | 8/1983 | Mettes et al. | 428/458 |

FOREIGN PATENT DOCUMENTS 0136892 8/1979 Fed. Rep. of Germany ........ 73/827

OTHER PUBLICATIONS

Bivins, "Peel Testing Metalized Films", Fall 1979, NASA Tech. Briefs, vol. 4, No. 3.
Baureis, Paper, Aug. 1983.

Primary Examiner—Stewart J. Levy
Assistant Examiner—Robert R. Raevis
Attorney, Agent, or Firm—Sprung Horn Kramer & Woods

[57] ABSTRACT

For an evaluation of the peel strength of a plastic sliding layer of a laminate for sliding surface bearings, which laminate comprises a steel backing, a porous sintered bronze layer on said steel backing, and a mixture of polytetrafluoroethylene which fills the pores of the bronze layer and constitutes a sliding layer on the bronze layer, the surface of the sliding layer of a sample that has been blanked from the laminate for sliding surface bearings is activated and adhesively joined to the end face of a testing bar of a testing apparatus in accordance with ISO Standard 4624. The ultimate tensile stress is then determined.

7 Claims, 1 Drawing Figure

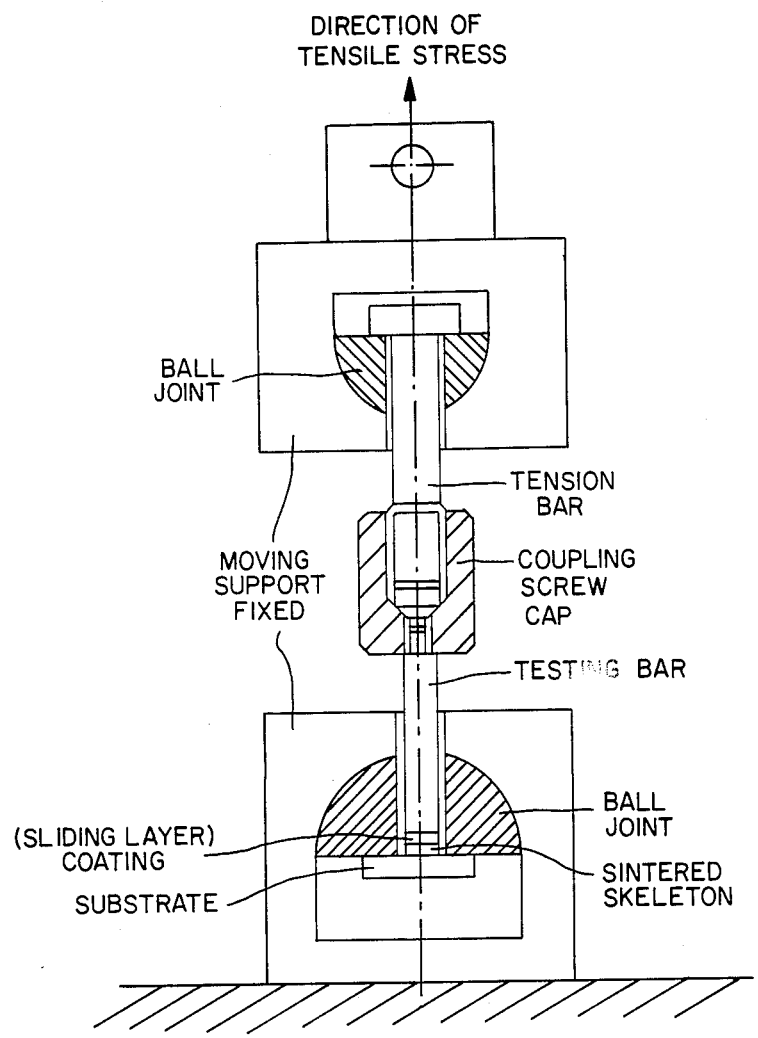

METHOD OF EVALUATING THE PEEL STRENGTH OF THE PLASTIC SLIDING LAYER OF A LAMINATE FOR SLIDING SURFACE BEARINGS

BACKGROUND OF THE INVENTION

The present invention relates to a method of evaluating the peel strength of the plastic sliding layer of a laminate for sliding surface bearings, which comprises a metallic backing layer consisting preferably of steel, a sintered or sprayed-on, porous bronze layer having a thickness of 0.1 to 1.0 mm and containing a rolled-in pore filler, and on said bronze layer a sliding layer having a thickness of 0.005 to 1.0 mm and made of perfluoro polymers, particularly polytetrafluorethylene, which may contain additives for improving the emergency running properties, such as lead, graphite, molybdenum disulfide, individually or in combination, and, if desired, also additives for improving the wear resistance and the load-carrying capacity, such as glass fibers, carbon fibers, glass beads, individually or in combination.

Laminates for sliding surface bearings constitute a combination of a metallic backing layer and a plastic sliding layer. As a rule, a sintered or sprayed-on, porous bronze layer consisting of tin bronze or tin-lead bronze and having a thickness of 0.1 to 5.0 mm is provided between the sliding layer and the metallic backing layer. The filler in the pores of the bronze layer and the sliding layer provided in a thickness of 0.01 to 0.5 mm on the bronze layer may consist of polymers, preferably of polytetrafluoroethylene, which may contain friction-reducing additives, such as lead, molybdenum disulfide and/or graphite, in an amount of 5 to 40 wt. %. The wear resistance and the load-carrying capacity may be improved by an addition of glass fibers, carbon fibers and/or glass beads in an amount of 5 to 40%. The porous bronze layer ensures a very strong bond between the plastic used and the metallic backing layer. The bond to the metallic backing layer ensures that the sliding surface bearing elements made from such laminates will be highly similar to sliding surface bearing elements made of metallic laminates as regards interference fit, elastic properties and thermal expansion so that they can be used with good results even if they have only a small wall thickness. Compared to all-plastic materials for sliding surface bearings, laminates for sliding surface bearings comprising a plastic sliding layer have the advantage that they have a higher thermal conductivity and a higher strength. The sliding surface bearing elements made from such laminates generally have a high load-carrying capacity up to about 150 N/mm$^2$.

Whereas, the laminates for sliding surface bearings of the kind described first hereinbefore were originally conceived for non-lubricated bearings, they are presently used also under conditions of mixed friction and with hydrodynamic lubrication owing to their excellent antifriction properties. For this reason they have a wide field of application. For instance, sliding surface elements made of such laminates are used in machines, motor vehicles, aircraft and apparatus and in electrical engineering. For this reason all those properties and features of laminates for sliding surface bearings which are required for bearings meeting specified requirements must be ensured by an extensive quality assurance program. One of the most important features which determine the quality of the laminate for sliding surface bearings is the peel strength of the plastic sliding layer on the porous bronze layer.

The peel strength of the plastic sliding layer has previously been evaluated by the cross hatch test used in accordance with DIN 53 151 for testing paints. In that test, a multiple-knife implement having six knife edges spaced 1 to 2 mm apart is used to form a sample of the laminate in a strip-shaped area with six incisions extending as far as to the bronze layer and in another strip-shaped area, which extends at right angles to the first, also with six of such incisions so that a grid of 25 squares is formed. After the grid has been made, a hand brush applied under a light pressure is reciprocated five times on the grid in both diagonal directions. The cross-hatched area is then inspected with a magnifying glass and is compared with illustrations and descriptions provided in an evaluating table so that a grid parameter is determined by which the peel strength of the sliding layer is defined. The cross hatch test has the disadvantage that errors in the evaluation cannot be avoided.

SUMMARY OF THE INVENTION

It is an object of the present invention to provide, for the evaluation of the strength of the sliding layer on the bronze layer or a laminate for sliding surface bearings of the kind described first hereinbefore, a testing method in which errors in evaluation are almost entirely precluded.

That object is accomplished in that the surface of the sliding layer of a sample punched from the laminate for sliding surface bearings is first mechanically and then chemically activated and is subsequently rinsed and dried and is adhesively joined to a mechanically roughened end face of a testing steel bar of a testing apparatus in accordance with ISO Standard 4624 and when the adhesive has cured the sliding layer is severed at the outside periphery of the testing bar as far as to the bronze layer, and the ultimate tensile stress is then determined in dependence on the tensile force required to separate the sliding layer from the bronze layer at right angles thereto, in accordance with ISO Standard 4624.

In a preferred embodiment of the method in accordance with the invention, the surface of the sliding layer of the punched sample is roughened in that an abrasive applied to said surface under a light pressure is reciprocated on said surface a plurality of times, preferably three to ten times, in two directions at right angles to each other.

In accordance with a further feature of the method in accordance with the invention, the surface of the sliding layer of the punched sample is activated in that the sample is dipped for 0.5 to 5 minutes into an etching solution which is suitable for perfluoro polymers.

The etching system employed suitably consists of a solution of liquid ammonia and sodium in accordance with German patent publication No. 12 60 778 or of tetrahydrofurane with sodium and naphthalene in accordance with German patent specification No. 10 16 869.

The stressing speed employed to determine the ultimate tensile stress is between 0.05 and 0.5 mm/s.

If metallic particles are contained in the sliding layer, the surface of the sliding layer is desirably demetallized by a treatment with an aqueous solution of acetic acid and hydrogen peroxide.

The apparatus for carrying out the method in accordance with the invention comprises, in accordance with ISO Standard 4624, a machine frame provided with a ball-jointed gripper which serves to grip the testing cylinder, and a ball-jointed spherical socket, which has a central aperture which is surrounded by an abutment for supporting the sample at its edge.

The invention will now be explained more in detail with reference to an illustrative embodiment.

BRIEF DESCRIPTION OF THE DRAWING

The FIGURE is an elevational view (partly in section) depicting a device for conducting the claimed method.

DETAILED DESCRIPTION OF THE INVENTION

A backing layer of steel was provided with a porous bronze layer, which has a thickness of 0.3 mm and consists of tin-lead bronze. In a rolling process, the pores of the bronze layer were completely filled with a mixture of polytetrafluoroethylene and lead was provided over the bronze layer. Samples which are 20 mm in diameter were punched from the strip laminate for sliding surface bearings and are then leveled on a toggle-joint press. The surface of the sliding layer was then roughened by means of an abrasive paper, which was applied under light pressure and reciprocated five times in two directions at right angles to each other. Lead was then removed from the surface of the sliding layer in an aqueous solution of acetic acid and hydrogen peroxide and thereafter the surface was chemically activated for 2 minutes in an etching solution of napthalene and sodium in tetrahydrofurane. When the sample had subsequently dried, the sliding surface was adhesively joined to the roughened end face of a testing cylinder of a testing apparatus in accordance with ISO Standard 4624; that cylinder was 10 mm in diameter. When the adhesive had cured, the sliding layer was severed as far as to the porous bronze layer around the outside diameter of the testing cylinder, the testing cylinder was gripped by the ball-jointed gripper of the testing apparatus in accordance with ISO Standard 4624, and that marginal portion of the sample which protruded beyond the diameter of the testing cylinder was applied to the abutment surrounding the aperture of a ball-jointed spherical socket. The tensile strength was then determined. The stressing speed amounted to 0.2 mm/s and the maximum tensile force in the area in which force was measured amounted to 1,500 N. The ultimate tensile stress A in $N/mm^2$ is calculated by the equation $$A = \frac{4F}{\pi d^2}$$

wherein
F = tensile force in N
d = diameter of testing bar in mm

In the case of a testing bar which is 10 mm in diameter, the ultimate tensile stress A can be calculated by the equation $$A = \frac{F}{78.54} \ (N/mm^2)$$

In addition to the determination of the ultimate tensile stress, the following scheme was used to describe the observed results:

A: The fracture has occurred between the sliding layer and the sintered skeleton. The velvetlike sliding layer is apparent on the surface of the testing cylinder and the pure bronze layer is apparent on the sample.

B: The fracture has occurred within the sliding layer. The plastic of the sliding layer is apparent on the surface of the testing cylinder and on the sample.

—/Y: The fracture has occurred between the sliding layer and the adhesive.

Y/Z: The fracture has occurred between the adhesive and the testing cylinder.

The ultimate tensile stress was found to amount to 3.0 $N/mm^2$. An inspection of the two surfaces of the fracture revealed that the fracture had occurred between the sliding layer and the bronze layer in about 80% of the area of the testing cylinder and between the sliding layer and the adhesive in 20% of the area. This gives the following result: 3.0 $N/mm^2$; 80% A, 20% —/Y.

It will be appreciated that the instant specification and claims are set forth by way of illustration and not limitation, and that various modifications and changes may be made without departing from the spirit and scope of the present invention.

What is claimed is:

1. A method of evaluating the pell strength of a plastic sliding layer of a laminate for sliding surface bearings, which comprises a metallic backing layer, a sintered or sprayed-on porous bronze layer having a thickness of 0.1 to 1.0 mm and containing a rolled-in pore filler and on said bronze layer a sliding layer having a thickness of 0.005 to 1.0 mm and made of perfluoro polymers, which may contain one or more first additives for improving the emergency running properties, said first additives selected from the group consisting of lead, graphite and molybdenum disulfide, individually or in combination, and, if desired, also one or more second additives for improving the wear resistance and the load-carrying capacity, said second additives selected from the group consisting of glass fibers, carbon fibers and glass beads, individually or in combination, the method comprising the steps of: first mechanically and then, chemically activating with a solution the surface of the sliding layer of a sample punched from the laminate for sliding surface bearings; subsequently drying the sample; adhesively joining the sample to a mechanically roughened end face of a testing steel cylinder of a testing apparatus in accordance with ISO Standard 4624; and when the adhesive has cured, severing the sliding layer at the outside periphery of the testing cylinder as far as to the bronze layer, and determining the ultimate tensile stress of a joint comprising the sliding layer in accordance with ISO Standard 4624.

2. The method according to claim 1, wherein the surface of the sliding layer of the sample is roughened wherein an abrasive is applied to said surface under a light pressure and is reciprocated on said surface a plurality of times in two directions at right angles to each other.

3. The method according to claim 2, wherein the abrasive is reciprocated three to ten times.

4. The method according to claim 1 or 2, wherein the surface of the sliding layer of the sample is activated by dipping the sample for 0.5 to 5 minutes into an etching solution which is suitable for perfluoro polymers.

5. The method according to claim 4, wherein the etching solution comprises one of a solution of liquid ammonia and sodium and a solution of tetrahydrofurane with naphthalene and sodium.

6. The method according to claim 1 or 2, for a metal-containing sliding layer, wherein the surface of the sample is demetallized by dipping the sample into an aqueous solution of acetic acid and hydrogen peroxide.

7. The method according to claim 1, wherein the ultimate tensile stress is determined at a stressing speed of 0.05 to 0.5 mm/s.

* * * * *